US010478321B2

United States Patent
Fischer et al.

(10) Patent No.: US 10,478,321 B2
(45) Date of Patent: Nov. 19, 2019

(54) VASCULAR IMPLANT WITH SIDE BRANCH

(71) Applicant: JOTEC GmbH, Hechingen (DE)

(72) Inventors: Heike Fischer, Meerbusch (DE); Juergen Merz, Balingen (DE)

(73) Assignee: JOTEC GmbH, Hechingen (DE)

( * ) Notice: Subject to any disclaimer, the term of this patent is extended or adjusted under 35 U.S.C. 154(b) by 0 days.

(21) Appl. No.: 14/717,934

(22) Filed: May 20, 2015

(65) Prior Publication Data

US 2015/0250626 A1 Sep. 10, 2015

Related U.S. Application Data

(63) Continuation of application No. PCT/EP2013/074367, filed on Nov. 21, 2013.

(30) Foreign Application Priority Data

Nov. 21, 2012 (DE) ........................ 10 2012 111 225

(51) Int. Cl.
*A61F 2/86* (2013.01)
*A61F 2/07* (2013.01)
(Continued)

(52) U.S. Cl.
CPC ................... *A61F 2/86* (2013.01); *A61F 2/07* (2013.01); *A61F 2/844* (2013.01); *A61F 2/856* (2013.01);
(Continued)

(58) Field of Classification Search
None
See application file for complete search history.

(56) References Cited

U.S. PATENT DOCUMENTS 7,615,072 B2 11/2009 Rust et al.
2001/0025195 A1* 9/2001 Shaolian ................. A61F 2/07
623/1.13
(Continued)

FOREIGN PATENT DOCUMENTS

EP 0 759 729 B1 1/2000
EP 2 522 305 A1 11/2012
(Continued)

OTHER PUBLICATIONS

International Search Report and Written Opinion mailed by the International Searching Authority dated Jul. 7, 2014 for PCT Application No. PCT/EP2013/074367 (untranslated, 11 pages).
(Continued)

*Primary Examiner* — Leslie Lopez
(74) *Attorney, Agent, or Firm* — Klarquist Sparkman, LLP (57) ABSTRACT

The present invention relates to a self-expanding vascular implant for implanting into a blood vessel of a patient. The vascular implant has a main body and at least one side body, and has integrally formed, one-piece stent springs, which are successively arranged in the longitudinal axis of the main body, with each stent spring meandering perpendicular to the longitudinal axis, and an implant material which is fixed to and connects the stent springs. The stent springs have pointed arches that alternately point toward the proximal end and the distal end of the main body and parallel to the longitudinal axis thereof. The at least one side body that branches off from the main body is, in the self-expanded state, set out at an angle relative to the longitudinal axis of the main body.

11 Claims, 5 Drawing Sheets

(51) Int. Cl.
  *A61F 2/844* (2013.01)
  *A61F 2/856* (2013.01)
  *A61F 2/06* (2013.01)
  *A61F 2/915* (2013.01)
  *A61F 2/89* (2013.01)
  *B21F 1/04* (2006.01)
  *B21F 45/00* (2006.01)
  *A61F 2/91* (2013.01)

(52) U.S. Cl.
  CPC .................. *A61F 2/91* (2013.01); *B21F 1/04* (2013.01); *B21F 45/008* (2013.01); *A61F 2/89* (2013.01); *A61F 2002/065* (2013.01); *A61F 2002/067* (2013.01); *A61F 2002/075* (2013.01); *A61F 2002/91508* (2013.01); *A61F 2002/91533* (2013.01); *Y10T 29/49613* (2015.01)

(56) References Cited

U.S. PATENT DOCUMENTS

| | | | |
|---|---|---|---|
| 2003/0208260 A1* | 11/2003 | Lau | A61F 2/07 623/1.15 |
| 2004/0117003 A1 | 6/2004 | Ouriel et al. | |
| 2006/0095118 A1* | 5/2006 | Hartley | A61F 2/07 623/1.35 |
| 2006/0287704 A1* | 12/2006 | Hartley | A61F 2/07 623/1.13 |
| 2007/0055347 A1* | 3/2007 | Arbefeuille | A61F 2/07 623/1.15 |
| 2007/0167955 A1 | 7/2007 | Arnault De La Menardiere et al. | |
| 2008/0195191 A1 | 8/2008 | Luo et al. | |
| 2010/0268327 A1* | 10/2010 | Bruszewski | A61F 2/07 623/1.18 |
| 2011/0218617 A1 | 9/2011 | Nguyen et al. | |
| 2011/0270380 A1 | 11/2011 | Bruszewski | |
| 2011/0301693 A1 | 12/2011 | Hartley et al. | |
| 2011/0319983 A1 | 12/2011 | Zhu et al. | |

FOREIGN PATENT DOCUMENTS

| | | |
|---|---|---|
| JP | 2004-049585 | 2/2004 |
| JP | 2008-526379 | 7/2008 |
| WO | WO 2006/076325 | 1/2006 |

OTHER PUBLICATIONS

First Examination report for Japanese Patent Application No. 2015-543423, dated Jul. 13, 2016.

Examination Report, dated Aug. 1, 2017, for corresponding Chinese Patent Application No. 2013800709064, with English-language translation.

Notification of Reasons for Rejection (with English translation), dated Jun. 20, 2017, for corresponding Japanese Patent Application No. 2015-543423, 15 pages.

* cited by examiner

Fig. 1

(Prior Art)

Fig. 5

VASCULAR IMPLANT WITH SIDE BRANCH

CROSS REFERENCE TO RELATED APPLICATIONS

This application is a continuation of international patent application PCT/EP2013/074367, filed on Nov. 21, 2013, designating the U.S., which international patent application has been published in German language and claims priority from German patent application DE 10 2012 111225.8, filed on Nov. 21, 2012. The entire contents of these priority applications are incorporated herein by reference.

BACKGROUND OF THE INVENTION

The present invention relates to a vascular implant for implanting into a blood vessel of a patient, the vascular implant being transformable from a compressed state into a self-expanded state, comprising a hollow-cylindrical main body with a proximal end and a distal end, a main body lumen and a longitudinal axis, and comprising a portion that has one-piece stent springs successively arranged over the longitudinal axis of the main body, respectively, and circumferentially meandering perpendicularly in relation to the longitudinal axis, respectively, and has an implant material fixed to the stent springs and connecting them, the stent springs only being connected to one another via the implant material and not between one another. The circumferentially meandering stent springs have pointed arches that face alternately toward the proximal end and the distal end of the main body and parallel to the longitudinal axis thereof. The vascular implant also has at least one hollow-cylindrical side body that branches off from the main body and comprises a side body lumen and a side body implant material, the side body lumen being in fluidic connection with the main body lumen.

Such so-called branched vascular implants are known in the prior art. Such vascular implants, which are also referred to as endovascular stents/stent grafts, are implanted for the treatment of aneurysms in arteries. An aneurysm is understood as being a widening or bulging of an arterial blood vessel as a result of congenital or acquired changes of the wall. The bulging may affect the vessel wall as a whole or, as in the case of a so-called false aneurysm or so-called dissection, blood can flow from the lumen of the artery in between the layers of the vessel wall and can tear them apart. Non-treatment of an aneurysm can lead to a rupture of the artery in the advanced stage, with the consequence that the patient internally bleeds.

For the treatment of aneurysms, the vessel concerned is therefore stabilized by implanting a stent/stent graft, in order to avoid rupturing of the vessel.

The stents/stent grafts or vascular implants that are used for the treatment of aneurysms generally consist in this case of a tubular/hollow-cylindrical metal frame, or of individual metal (stent) springs successively arranged, the jacket surface of which is covered with a textile or polymer film, resulting in a hollow-cylindrical body. For implantation, this stent/stent graft is then radially compressed, for example by means of a sheath surrounding and compressing it, so that its cross section is reduced significantly. Then, with the aid of an insertion system, the stent/stent graft is brought into the region of the aneurysm, where the stent is released. Due to the resilience of the metal frame or the metal springs, the stent expands again into its original form, thereby spreading its jacket surface, which becomes clamped internally in the blood vessel proximally and distally with respect to the aneurysm. In this way, the blood can now flow through the stent/stent graft, whereby further loading of the bulging is prevented.

The expansion of the metal frame or the metal elements may in this case be effected, on the one hand, by using self-expanding metal, such as for example nitinol, or else by using a dilation balloon, which is inserted internally into the metal frame, the dilation of which expands the metal frame/the metal elements.

At the location of the vessel at which a stent/stent graft or such a vascular implant is to be inserted, blood vessels often branch off laterally, which is why upon introduction of the vascular implant at such branching locations in the vessel there is the risk of these side vessels being cut off from blood supply by the vascular implant in the main vessel or by the implant material, which can be impermeable to blood. Therefore, in these regions vascular implants often have openings—known as "fenestrations"—in the jacket material or the implant material, in order to direct blood flowing through the vascular implant through these openings and also generally through side branches of the vascular implant, which side branches are separately provided in these openings and are being introduced into the side vessels, also into the side vessels branching off from the vessel. In this way, it is guaranteed that the regions of the body that are supplied by the side vessel are supplied with blood also.

In many cases, the vascular implants or stent/stent grafts to be introduced at such branching regions do not only have fenestrations but also side branches branching off from the main body of the vascular implant, these branches being released in the aneurysmal sac above the branching vessel and serving, for example, as a landing zone for an additional stent graft, which is implanted into the side branch and the branching vessel in order to bridge the aneurysm. In this way it is additionally guaranteed that the side vessels are supplied with blood also.

Critical regions in the human vascular system are, for example, the region of the aorta bifurcation, and also the branching of the Arteriae iliacae communes into the Arteriae iliacae externa and the Arteriae iliacae interna. With each of the branchings, it is usually necessary to ensure the supply to the vessels branching off if the aorta or the Arteriae iliacae have to be treated in this region, for example because of an aneurysm. Presently, in the prior art, for the treatment of abdominal aneurysms stents or stent grafts (together also known as "vascular implants") are used that consist of a main body with two legs extending distally, which are intended for placement in the Arteriae iliacae communes. Because of its form and placement, such a vascular implant is also referred to as an Y prosthesis.

In the case of many of these implants, the second leg, which is also referred to as the contralateral leg, is inserted separately from the main body, and only after the placement of the main body, in order to facilitate overall placement of the prosthesis. Correspondingly, in the case of this implant, first the main body is deployed by way of a—generally—transfemoral access above the aorta bifurcation. In a second step, a further implant, that is to say the contralateral leg, is then engaged with the main body, thus completing the bifurcation prosthesis.

Vascular implants comprising side branches that are currently known and available in the prior art are usually made either by attaching the side branches d between the stent springs or else by placing the side branches between the pointed arches. A disadvantage of the vascular implants bearing side branches that are known in the prior art is that these vascular implants having side branches usually have an accumulation of material in the region of the branching, such as for example a nitinol ring in the side branch, by means of which the side branch is opened after expansion, or such as for example additionally sewn-in fabric rings of implant material, which in turn necessitate larger insertion systems, and, in narrow vessels, may lead to difficult handling of these vascular implants. The side branches are additionally also very unstable and, as a result, difficult to handle once they have been introduced into the vessel.

SUMMARY OF THE DISCLOSURE

The object of the present invention is therefore to provide a vascular implant that can be inserted easily and stably into the main vessel and into the side vessel, and consequently into the branching, whereby an accumulation of material is advantageously avoided and an undisturbed flow of blood is achieved.

This object is achieved according to the invention by a development of the vascular implant mentioned at the outset, in which, in the self-expanded state, the at least one side body branching off from the main body is set out at an angle in relation to the longitudinal axis of the main body, the angle being effected by at least one pointed arch of a stent spring of the main body, in the self-expanded state, angularly protruding in relation to the longitudinal axis of the main body in a preformed way.

This object is also achieved by a method for producing such a vascular implant.

The object on which the invention is based is achieved completely in this way.

The preformed protruding of at least one pointed arch of one of the stent springs angularly in relation to the longitudinal axis of the main body achieves the effect that the side branch is automatically set up, which is specifically due to the spring force of the at least one pointed arch of at least one stent spring in the predetermined form, which arch is protruding in a preformed way. In this case, the angle at which the at least one side protrudes can be predetermined through the production process. In this way, surplus material, with the aid of which the side body was previously set up, can be avoided in the region of the at least one side body, and at the same time the insertion of the bridging stent graft into the side vessel is significantly facilitated. The self setting-out/protruding of the side body is achieved by the vascular implant according to the invention being inserted in a compressed state into the vessel to be treated or into the branching region, and the self-expanding vascular implant being able to expand after removal of the sheath or the compressing means, whereby the at least one set-out pointed arch is also set up, and consequently can deploy the side body. The other pointed arches of the at least one stent spring in this case run parallel to the longitudinal axis of the main body of the vascular implant. They consequently do not protrude angularly in relation to the longitudinal axis of the vascular implant.

As discussed at the beginning, presently, a "stent spring" is understood as being any one-piece, annular element which is compressible due to its material, and which, after removal of the compressing pressure, can expand again in the manner of a spring. "Meandering" is understood in the present case as meaning any serpentine or looped shape of the stent spring or the stent wire, each stent spring being formed as one part, i.e. from one stent spring ring circumferentially meandering manner.

In this context, a "one-piece stent spring circumferentially meandering", presently, is an annular stent element that expands and can be compressed in a spring-like manner and is circumferential and meandering, wherein the wave crest and wave trough, which form a phase, alternate.

Advantageously, in this case a pointed arch is respectively formed by two legs and a vertex or lowest point thereinbetween.

"At least one pointed arch" presently means that the side body is extended by the protrusion or setting out of a single pointed arch of a stent spring, or else by two or more pointed arches. In a preferred embodiment, two pointed arches of a stent spring are set out. In principle, the plurality of the pointed arches circumferentially meandering form the stent spring of the main body, and the protruding pointed arch/pointed arches form(s) the branching point for the side body.

In the present case, "proximal" generally denotes the position, direction or a portion or end of a component of the vascular implant that lies closest to the heart of the patient to be treated.

Correspondingly, in the present case, "distal" denotes that position, direction or a portion or end of a component of the vascular implant according to the invention that is/leads further/furthest away from the heart of a patient.

Correspondingly, in the present case, the "proximal" opening and the "distal" opening of the vascular implant are the openings ensuring blood flow through the hollow-cylindrical body of the vascular implant: when the vascular implant according to the invention is implanted into a blood vessel, such as for example the aorta, the blood coming from the heart, thus, flows through the proximal opening of the vascular implant, and leaves the vascular implant through its distal openings.

The vascular implant or its hollow-cylindrical main body may have a uniform diameter, or else different diameters, over its overall length.

By definition, the stent springs are not directly connected to one another, and do not have any connecting legs or struts or similar connecting elements therebetween. The stent springs are only connected to one another by way of the implant material to which the stent springs are attached, whereby an "indirect connection" is created between the stent springs.

In the present case, a "stent" denotes any device or a structure that provides a force of expansion and/or a supporting function for a prosthesis.

Presently, the expression "stent graft" is intended—as also in the prior art—to encompass a prosthesis that has one or more stents (or stent springs) and also an implant ("graft") material connected thereto, which forms a lumen through at least one portion of the prosthesis.

According to a further embodiment of the vascular implant according to the invention, it is preferred if the angle with which the at least one side body protrudes from the main body with respect to the longitudinal axis of the main body is between 20° and 90°, is 20° and 90°, and in particular between 35° and 55°, and in particular angles in the range of 40° to 50°, and still more preferably in the range between 44° and 46°, and preferably 45°. It goes without saying that the vascular implant according to the invention may also comprise several side bodies, each protruding at different angles in relation to the longitudinal axis of the vascular implant.

In the present case, this consequently also expressly includes all figures that lie between these ranges; it will be clear to a person skilled in the art that the ranges mentioned herein above also include tolerance bands that lie outside, i.e. above or below, the ranges specified, and lie within customary production and measuring tolerances.

The angle at which the at least one side body is set out/protrudes from the main body is in this case specifically made to match the vessel to be treated or the vessel portion to be treated. This can be defined exactly in advance by the doctor performing the treatment. It goes without saying that, according to a further embodiment of the vascular implant according to the invention, the respective precise angle may vary from vascular implant to vascular implant. In general, due to the stent spring with the at least one pointed arch protruding at an angle, the position of the side branch is more flexible in vivo than if it is implemented without an angle. There is less risk of the side branch kinking.

According to a development of an embodiment of the vascular implant according to the invention, the at least one side body has—perpendicularly in relation to its side-body longitudinal axis—a portion with at least one side-body stent spring circumferentially meandering and a side-body implant material fixed to the side-body stent spring and the stent spring of the main body angularly protruding, thus connecting them, wherein the at least one side-body stent spring and the stent spring of the main body angularly protruding are only being connected via the side-body implant material and not with one another.

This embodiment has the advantage that the at least one side body of the vascular implant according to the invention also has a stented portion, which ensures secure anchorage for a second stent graft, which leads into the branching vessel to bridge the aneurysmal sac.

In the present case, a "stented portion" is understood as to encompass any portion of a vascular implant that has at least one stent or a stent spring element connected with a prosthetic material.

By contrast thereto, in the present case an "unstented" portion is understood as meaning any portion of a vascular implant that is only formed from prosthetic material.

According to a further embodiment of the vascular implant according to the invention, the main body and/or the at least one side body may have—along with the first stented portion—at least one additional unstented portion and/or a portion with a braided or lasered stent/stent graft, the second portion adjoining the stented portion proximally or distally. "An additional unstented portion" presently means that the portion is provided as a proximal or distal extension of the main body lumen or of the side branch, whereby the stented or unstented portion is either being inserted in vivo after implantation of the vascular implant as an element that is separate from the main body, or else is being fixedly connected to the vascular implant. This embodiment has the advantage that the side branch can be extended into the branching vessel, for example the Iliaca interna, in order for example to exclude the aneurysm from the blood pressure. In this way, the braided or lasered stent graft can seal off the aneurysm in the side vessel and in the landing zone of the Iliaca interna.

When an unstented portion is used, it may be sewn to the vessel wall, which is advantageous in particular in the case of vascular implants that are intended to be immovably attached in the vessel.

If a portion with a braided supporting stent is provided, the braided stent may either be used in connection with an implant material, and be introduced internally into the implant material, whereby the latter is likewise pressed against the wall of the vessel by the expansion of the wire mesh and anchored there. Or else the wire mesh may be sewn to the implant material.

In addition, the main body and/or the at least one side body may also have a stent portion that is free from implant material, this stent portion then preferably being formed from a wire mesh, and only—also—providing for the anchoring of the vascular implant in the blood vessel.

According to a development of the vascular-implant stent spring according to the invention, it is preferred if at least three legs, which connect a first vertex, a first lowest point circumferentially following the first vertex, a second vertex circumferentially following the first lowest point, and a second lowest point circumferentially following the second vertex, respectively, have different lengths.

This embodiment has the advantage that the overall shape of a stent spring is asymmetrical, thus avoiding kinking of the vascular implant as a whole. The stent spring consequently has irregular "amplitudes", i.e. the pointed arches—or "wave crests"/"wave troughs"—vary in their height or depth on account of the legs of varying length. It goes without saying that the legs of the pointed arches of a stent spring—as a whole—may have different lengths, or else indeed may only have three or more than three of different lengths. The relative distances between a vertex and a lowest point or between all of the vertices and the lowest points of a stent spring may also vary.

As a consequence, with the embodiment described above, the circumferentially meandering stent springs have an asymmetrical shape, a shape in which two successive wave crests, respectively, have different heights, and, as a consequence, also the wave troughs lying therebetween have different depths, respectively. Altogether, therefore, in an alternating manner in circumferential direction, a higher wave crest/vertex is followed by a wave crest/vertex that is lower or less high than the previous wave crest/vertex, and this wave crest/vertex is again followed by a wave crest/vertex that is higher than the wave crest/vertex directly before it, and so on, whereby wave troughs/lowest points of respectively varying depth are lying between the wave crests/vertices of varying height: also with respect to the wave troughs/lowest points, a lower wave trough/lowest point is again followed—in an alternating manner in the circumferential direction—by a wave trough/lowest point that is less low than the wave trough/lowest point arranged directly before it in circumferential direction, and this wave trough/lowest point is again followed by a wave trough/lowest point that is lower than the one before it. In other words, a stent spring therefore has pointed arches with at least two or three lowest points of varying depth, the "different depths" relating to an imaginary line which is perpendicularly and circumferential in relation to the longitudinal axis of the hollow-cylindrical main body and which connects the lowest lowest points with one another. By definition, consequently, less low lowest points do not lie on this imaginary line, and the same applies in turn to the vertices.

According to a further embodiment, it is also preferred if at least two stent springs successively arranged over the longitudinal axis are arranged with respect to the longitudinal axis of the hollow-cylindrical main body and with respect to one another in such a way that the lowest points of the pointed arches of a first stent spring, respectively, lie opposite the vertices of pointed arches of a second stent spring arranged after the first stent spring over the longitudinal axis of the vascular implant at a distance and at an imaginary line that is parallel to the longitudinal axis of the vascular implant, and such that a lowest lowest point of a pointed arch of the first stent spring lies opposite a vertex of the second stent spring arranged distally thereafter, at a distance, this vertex being less high than a highest vertex of the second stent spring; correspondingly, in this embodiment a less low lowest point—that is to say a lowest point that is less low than a lowest low point of the first stent spring—thus also always comes to lie at a distance from and opposite a highest vertex of the second stent spring arranged distally thereafter, which highest vertex is higher than a less high vertex of the second stent spring.

With this embodiment two different bending planes between the pointed arches lying adjacently opposite are effected, thus rendering the vascular implant significantly more flexible, while retaining its longitudinal stability. At the same time, it can be bent in a number of planes without kinking. It goes without saying that with other embodiments of the asymmetrical stent spring according to the invention also more than two bending planes can be effected.

In addition to the different leg LENGTHS, this phase arrangement of at least two, preferably all, of the stent springs also provides the vascular implant with an asymmetrical pattern, which very efficiently contributes avoiding of kinking.

Correspondingly, in another embodiment of the vascular implant according to the invention, at least two stent springs successively arranged over the longitudinal axis, respectively, have legs of different lengths for forming the pointed arches of varying height circumferentially arranged, with higher pointed arches and shorter pointed arches, and a higher pointed arch, facing toward the proximal direction x of a first stent spring lies opposite a shorter pointed arch facing toward the distal direction y of a second stent spring arranged proximally thereafter, at a distance and in an imaginary line that is parallel to the longitudinal axis of the vascular implant, and/or that a shorter pointed arch, facing toward the proximal direction x, of a first stent spring lies opposite a longer pointed arch, facing toward the distal direction y, of a second stent spring arranged thereafter in the proximal direction x, at a distance and in an imaginary line that is parallel to the longitudinal axis of the vascular implant.

Also, with this embodiment of the individual stent springs and their arrangement in relation to one another an asymmetrical stent spring shape can be achieved.

Due to the legs of varying length, pointed arches of varying height are obtained, their height being determined with respect to an imaginary line running in the circumferential direction of the stent spring and perpendicular in relation to the longitudinal axis of the vascular implant through the highest vertex/vertices of the pointed arches facing toward the proximal direction. This design and definition mean that there are always vertices that lie under this imaginary line through the highest vertices, and consequently represent vertices that are shorter than the highest vertices. By analogy, this also applies with respect to the pointed arches or the lowest points facing towrad the distal direction: here, too, an imaginary line in the circumferential direction of a stent spring is running through the highest vertex/vertices of the pointed arches facing in the distal direction, so that there are higher and shorter vertices of the pointed arches facing toward the distal direction.

Exemplary heights for the various pointed arches lie for example in the range from 4 to 18 mm, preferably about 8 mm to 14 mm, for the highest pointed arches, that is to say for the pointed arches that are higher than shorter pointed arches, and from 4 to 10 mm, preferably 6 mm to 8 mm, for the shorter pointed arches. One skilled in the art will readily understand that a stent spring, on the one hand, may have pointed arches with at least two or three or four or more pointed arches of varying height. If there are three pointed arches of varying height, a stent spring therefore has three different heights for the pointed arches, that is to say at least a first higher pointed arch, the height of which is the highest, at least a second pointed arch, the height of which is shorter than that of the first pointed arch, and a third pointed arch, the height of which is, again, shorter than that of the second pointed arch, etc. Heights that can be given by way of example, serving in the present case merely for exemplary purposes and not intended to be limiting, are for example 10 mm (higher pointed arches) and 8 mm (shorter pointed arches); 12 mm (higher pointed arches) and 8 mm (shorter pointed arches); 12 mm (higher pointed arches) and 9 mm (shorter pointed arches); 12 mm (higher pointed arches) and 10 mm (shorter pointed arches); 16 mm (higher pointed arches) and 14 mm (shorter pointed arches), 16 mm (higher pointed arches) and 13 mm (shorter pointed arches); 16 mm (higher pointed arches), 12 mm (shorter pointed arches) and 10 mm (still shorter pointed arches); 10 mm (higher pointed arches) and 8 mm (shorter pointed arches); 12 mm (higher pointed arches), 10 mm (shorter pointed arches) and 8 mm (still shorter pointed arches).

Presently and throughout the description, the term "about" is intended to mean that the indications given for ranges and numbers are also intended to include those that are included by a person skilled in the art on account of measuring differences or tolerances and are suitable for achieving or helping to achieve the object the invention is based upon.

In general, the kinking of a vascular implant, in particular in regions in which blood vessels are curved, is critical, since kinking curved regions can cause a blocked or disturbed/turbulence-affected or reduced blood flow or even a stop of blood flow.

This can be successfully prevented by the embodiments according to the invention of the vascular implant with asymmetrical stent springs.

According to an embodiment of the vascular implant according to the invention, it is preferred if the self-expanding vascular implant according to the invention has at least three stent springs, successively arranged over the longitudinal axis, which are not directly connected to one another, but only connected to one another via the implant material.

According to a further embodiment, it is preferred if the vascular implant according to the invention has between three and ten, preferably three, four, five, six, seven, eight, nine or ten, stent springs successively arranged.

The number of stent springs will depend on the required length of the vascular implant to be used, or on the vascular defects to be bridged of a patient.

According to a development of the vascular implant according to the invention, the stent springs are connected to the implant material indirectly connecting them, preferably being sewn to the implant material. The same also applies to the stent springs of the side body. In this case, the stent springs may either be sewn in the internal lumen of the vascular implant, i.e. internally to the implant material, or else externally onto the implant material.

Suture materials currently used in the fields of surgery and stent implant technology can be used as suture material for sewing the stent springs to the implant material, and such suture materials generally consist of polyester, polyurethane, polytetrafluoroethylene, polyethylene, ultrahigh molecular weight polyethylene (UHMWPE), polypropylene.

According to a preferred embodiment of the vascular implant according to the invention, it has between one four, i.e. one, two, three or four, side branches set up/protruding at an angle from the main body.

Consequently, the vascular implants according to the invention can also be advantageously introduced into vessel portions at which a number of side blood vessels branch off. Depending on the respective patient or vascular situation, one skilled in the art will be able to determine how many side branches are required for the vascular implant to be used.

It goes without saying that an individual stent spring may have several protruding pointed arches, thus forming several side branches, or else the protruding pointed arches are provided on different stent springs, depending on the position of the branching side blood vessels.

Furthermore, the present invention also relates to a method for producing a vascular implant according to the invention, the method having the following steps:

providing a fitting, which is generally has a cylindrical main body and a fitting element, which element protrudes at an angle from the cylindrical main body and is connected to the fitting and which has a rounded inclined face, wherein the fitting also has pin-like elements in the position of vertices of stent springs circumferentially meandering, providing a stent-spring-forming wire, preferably of nitinol, winding, under tension, the stent-spring-forming wire on the fitting over the pin-like elements, such, that stent springs with pointed arches circumferentially meandering are wound around the fitting and are fixed on the fitting, the at least one pointed arch set out/protruding at an angle being formed on the fitting element protruding at an angle.

In further consecutive steps, the stent spring formed by the steps of the method according to the invention can be sintered in a thermal bath, thereby permanently retaining its predetermined form.

In further consecutive steps, the wire ends may be connected by a crimping tube, and the surface of the stent spring thus produced may be subsequently electropolished.

By such shaping of the stent spring, with the aid of which the side body can be set up, it is ensured that the stent spring has at least one pointed arch, preferably two pointed arches, which is/are set up in relation to the longitudinal axis of the vascular implant, namely at an angle that depends on the fitting element protruding at an angle, or, in other words, depending on the angle that is formed by its surface being inclined with respect to the cylindrical main body.

The angle may in this case be set such that the side branch is set up in a preferred way within the aneurysm, and, thus, a secure bridging of the aneurysmal sac into the branching vessel is achieved, as the case may be by means of a second stent graft. Due to the setting up of the side branch a sufficient blood flow through the latter and the possibly extended stent graft into the branching vessel is being achieved.

Just like the other stent springs provided in the vascular implant according to the invention, the stent spring with the pointed arch protruding at an angle is preferably formed from a shape-memory metal, preferably nitinol, on the fitting and is subjected to a heat treatment for fixing its expanded form.

In a vascular implant according to the invention, the stent spring formed by the method according to the invention can be used as the stent spring providing a pointed arch protruding at an angle for the side branch which is then likewise protruding at an angle. In short, the stent spring produced according to the invention is fixed, preferably sewn, together with additional stent springs without pointed arches protruding at an angle to an implant material at distances from one another for forming the hollow-cylindrical main body. The pointed arch protruding at an angle may then also be fixed, preferably sewn, to an implant material, for example with another stent spring, for forming the side branch.

Further advantages and features can be derived from the following description and the accompanying drawing.

It goes without saying that the features mentioned above and still to be explained below can be used not only in the combination respectively specified, but also in other combinations or on their own without departing from the scope of the present invention.

BRIEF DESCRIPTION OF THE DRAWINGS

An exemplary embodiment of the invention is represented in the drawing and is described in more detail below with reference thereto. In the drawing:

FIGS. 2A and 2B show an exemplary embodiment of the vascular implant according to the invention with a side body; FIG. 2A: in a spatial lateral plan view; FIG. 2B: in a schematic lateral plan view;

DESCRIPTION OF PREFERRED EMBODIMENTS

Figure 1:
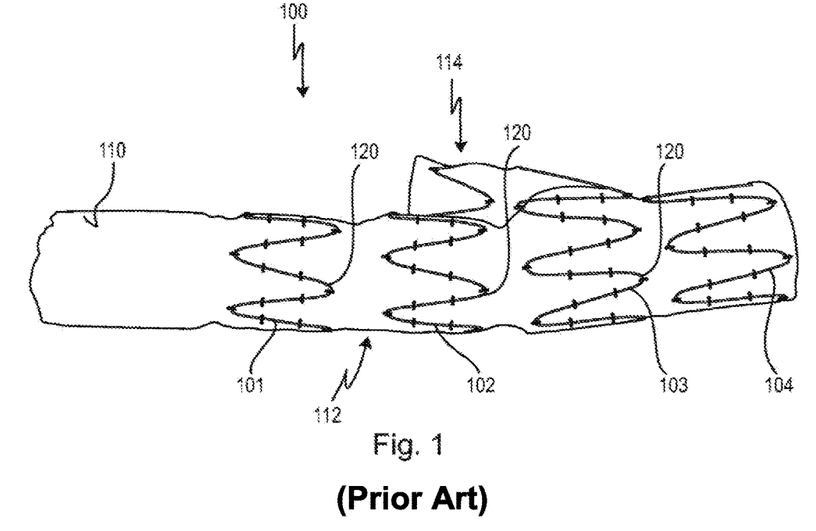
FIG. 1 shows an exemplary embodiment of a vascular implant of the prior art having a side body.

In FIG. 1, a vascular implant 100 from the prior art is shown, which has four stent springs 101, 102, 103, 104 successively arranged, the phases of the stent springs 101, 102, 103, 104 running symmetrically in relation to one another: here, a vertex 120 of a first stent spring 102 and a vertex of the second stent spring 103, following distally thereafter, lie exactly opposite in the longitudinal axis, so that the stent springs 101, 102, 103 and 104 together form a symmetrical pattern on an implant material 110. The vascular implant 100 has a main body 112 and a side body 114, which branches away from the main body 112 and is sewn onto the latter via the implant material 110. Due to an accumulation of material in the branching region, the side body 114 protrudes slightly from the main body 112.

Figure 2A:
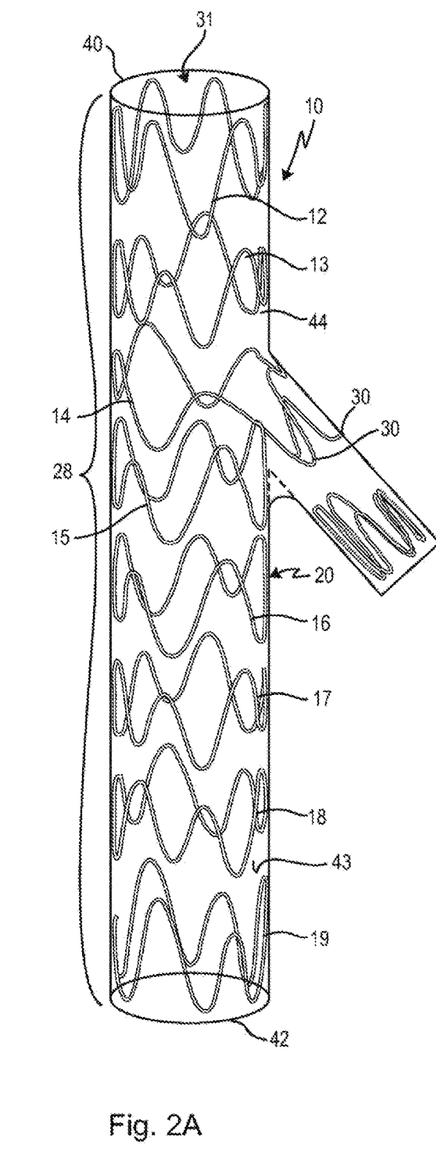
Figure 2B:
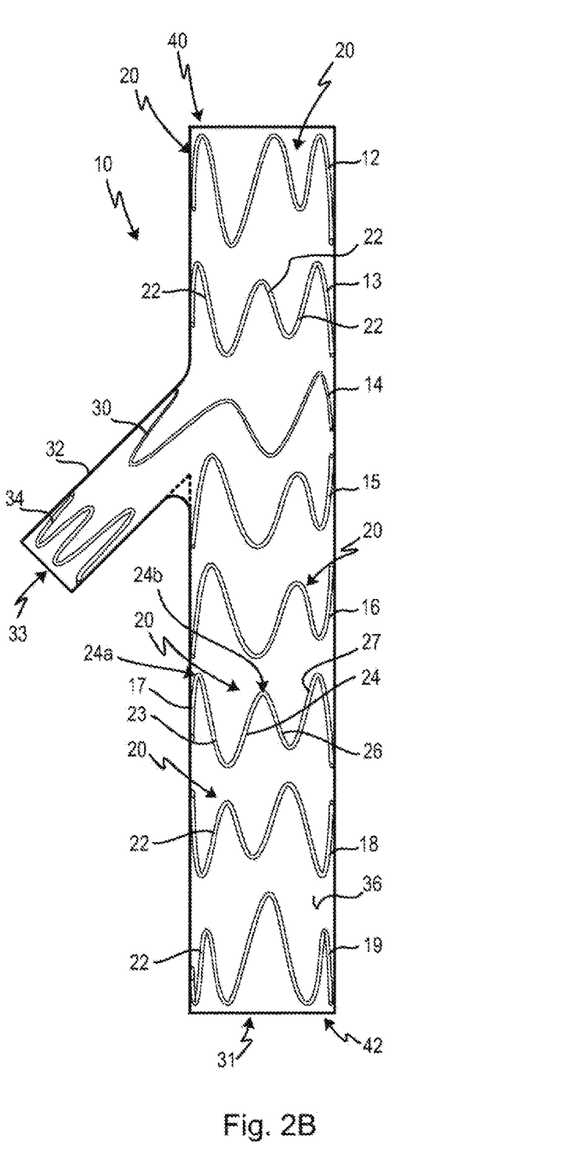

FIGS. 2A and 2B overall show an exemplary embodiment of a vascular implant 10 according to the invention, with, by way of example, eight stent springs 12, 13, 14, 15, 16, 17, 18 and 19 successively arranged over the longitudinal axis of the vascular implant 10.

FIGS. 2A and 2B also show that the individual stent springs 12 to 19 have pointed arches 20 arranged in different phases. In FIGS. 2A and 2B the elements of the stent spring 18 are provided with reference numbers by way of example, it being self-evident that the stent springs 12, 13, 14, 15, 16, 17 and 19 are constructed analogously, and the element designation with reference numbers has only been omitted from these for purposes of clarity. As shown in FIG. 2A with reference to stent spring 18, a pointed arch 20 is respectively formed by two legs 22, 23, 26, 27 and either a vertex 24a or a lowest point 25a. A pointed arch 20, facing toward the proximal end 40 of the main body 44, has by definition at least one vertex 24a; a pointed arch 20, facing the distal end, has by definition a lowest point 25a.

The vascular implant 10 additionally has a proximal end 40 and a distal end 42. The stent springs 12, 13, 14, 15, 16, 17, 18 and 19 are connected to one another indirectly by an implant material 43—i.e. not directly by way of struts or the like —, so that the vascular implant has a hollow-cylindrical main body 44 with a main body lumen 31, the diameter of which may or may not change over the length. The vascular implant shown in FIGS. 2A and 2B therefore has a portion 28 that is "stented", or it consists of such a portion, since all of the implant material 43 is supported by stent springs 12 to 19 that are attached to the implant material 43 at specific distances from one another. It goes without saying that the vascular implant 10 may also have further portions that consist either of an implant material supported by a stent wire mesh or a laser-cut stent, or of an unstented implant material, or of a stent wire mesh without implant material.

As mentioned further above, the stent springs 12, 13, 14, 15, 16, 17, 18 and 19 of the exemplary embodiment shown in FIGS. 2A and 2B of the vascular implant 10 according to the invention have pointed arches 20, with vertices 24a and lowest points 25a and also with legs 23, 24, 26, 27 connecting them. FIGS. 2A and 2B also reveal that in each case three legs 22, 23, 24 following one another in the circumferential direction of the stent spring 18, which connect a low point 25b to a vertex 24a (leg 22), the vertex 24a to the lowest point 25a (leg 23) and the lowest point 25a to the vertex 24c (leg 24), have different lengths: here, the length of the leg 22 is in shorter than the length of the leg 23, and the length of the leg 24 is again longer than the length of the leg 23. Due to the alternately different lengths of the legs 22, 23, 24, 26, 27, the meandering shape of the stent springs 12, 13, 14, 15, 16, 17, 18 and 19, or their vertices 24a, 24b, 24c and lowest points 25a, 25b, 25c, are not uniform: the pointed arches 20 of a stent spring 12, 13, 14, 15, 16, 17, 18 and 19 do not have the same height—in relation to an imaginary line in the circumferential direction that is made to pass through the vertices—, but form different phases on account of the vertices and lowest points 24a, 24b, 24c, 25a, 25b, 25c of varying height. As a result, the stent springs 12, 13, 14, 15, 16, 17, 18 and 19 are, as it were, asymmetrical.

In other words, the pointed arches 20, which because of their form are also referred to here as "wave crests"/"wave troughs", vary in height or depth due to the legs 22, 23, 24 having varying length. With the asymmetrical meandering shape of the circumferential stent springs 12, 13, 14, 15, 16, 17, 18, 19, two successive pointed arches facing toward the proximal direction, thus, respectively have different heights, seen in relation to an imaginary straight line that connects the lowest low points 25b and 25c with one another, and consequently also the pointed arches, facing toward the distal direction, lying respectively in between have different depths.

In addition, in the exemplary embodiment shown in FIGS. 2A and 2B, the stent springs 12, 13, 14, 15, 16, 17, 18 and 19 are successively arranged over the longitudinal axis, such, that an additional asymmetry is formed, which is also explained in more detail below in FIG. 5.

Figure 5:
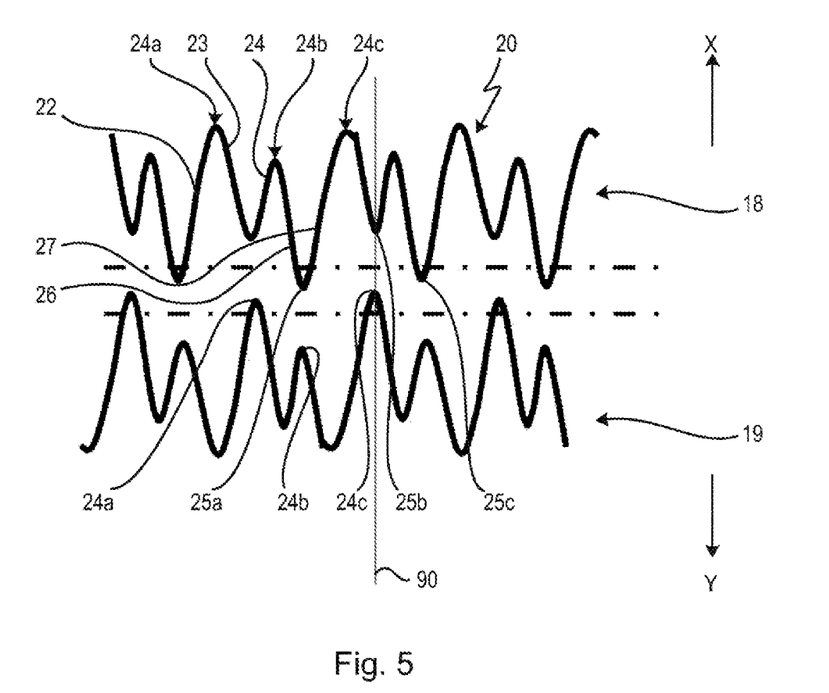
FIG. 5 shows a partial and schematic representation of the shape of two stent springs arranged after over the longitudinal axis of the vascular implant, as they may be implemented in an exemplary embodiment of a vascular implant according to the invention.

FIG. 5 shows a schematic, partial representation of two asymmetrical stent springs 18, 19 according to the invention. There, again, the principle of the asymmetrical stent springs is shown in a simpler form, as it may be implemented in accordance with an embodiment of the vascular implant according to the invention: the stent springs 18, 19, respectively, have pointed arches 20 that alternately face toward the proximal and distal direction, and thereby form wave crests and wave troughs. The leg 22, vertex 24a and the leg 23 thereby form a pointed arch facing toward the proximal direction X, and the leg 23, the lowest point 25a and the leg 24 form a pointed arch facing toward the distal direction Y. Due to the different lengths of the legs 22, 23, 24, 26, 27 following one another, the pointed arches have different heights and depths, which can be seen from the vertices 24a, 24b of varying height and the lowest points 25a, 25b of varying depth, the height or depth of which is dimensioned on the basis of an imaginary circumferential line perpendicular to the longitudinal axis of the vascular implant. Thus, in the circumferential direction, a higher vertex 24a is followed by a vertex 24b that is lower or less high than the previous vertex 24a, and this vertex 24b is again followed by a vertex 24c that is higher than the vertex 24b directly before it, and so on, lowest points 25a, 25b, 25c of respectively varying depth lying between the vertices 24a, 24b, 24c of varying height: also with respect to the lowest points 25a, 25b, 25c, a lower lowest point 25a is again followed in an alternating manner in the circumferential direction by a lowest point 25b that is less low than the lowest point 25a arranged directly before it in the circumferential direction, and this lowest point 25b is again followed by a lowest point 25c that is lower than the one before it. In other words, a stent spring 18, 19 therefore has pointed arches 20 with at least two or three lowest points 25a, 25b, 25c of varying depth, the different depths relating to an imaginary line that circumferentially runs perpendicularly in relation to the longitudinal axis of the hollow-cylindrical main body and connects the lowest lowest points 25a, 25c with one another. By definition, consequently, less low lowest points 25b do not lie on this imaginary line, and the same applies in turn to the vertices.

As also shown in FIG. 5, the two stent springs 18, 19 successively arranged over the longitudinal axis are arranged with respect to the longitudinal axis of the hollow-cylindrical main body and with respect to one another, such, that the lowest points 25a, 25b, 25c of the pointed arches 20 of a first stent spring 18 respectively lie opposite the vertices 24a, 24b, 24c of pointed arches 20 of a second stent spring 19 arranged after the first stent spring 18 in the longitudinal axis of the vascular implant 10, at a distance and in an imaginary line 90 that is parallel to the longitudinal axis of the vascular implant 10, to be precise in such a way that a lowest lowest point 25a of a pointed arch 20 of the first stent spring 18 lies opposite a vertex 24b of the second stent spring 19 arranged distally thereafter, at a distance, this vertex 24b being less high than a highest vertex 24a of the second stent spring 19; correspondingly, in the case of this embodiment a less low lowest point 25b—that is to say a lowest point 25b that is less low than a lowest low point 25a of the first stent spring 18—thus also always comes to lie at a distance from and opposite a highest vertex 24c of the second stent spring 19 arranged distally thereafter, which highest vertex 24c is higher than a less high vertex 24b of the second stent spring 19.

In other words, FIG. 5 shows an example of the embodiment of stent springs of the vascular implant according to the invention in which embodiment at least two stent springs 18, 19 successively arranged over the longitudinal axis, respectively, have legs 22, 23, 24 of different lengths for forming of pointed arches 24a, 24b, 24c; 25a, 25b, 25c of varying height and successively and circumferentially arranged, with higher pointed arches 24a, 24c; 25a, 25c and shorter pointed arches 24b; 25b, and that a higher pointed arch 24a, facing in the proximal direction x, of a first stent spring 19 lies opposite a shorter pointed arch 25b, facing in the distal direction y, of a second stent spring 18 arranged thereafter in the proximal direction X, at a distance and in an imaginary line 90 that is parallel to the longitudinal axis of the vascular implant 10, and/or that a shorter pointed arch (24b), facing in the proximal direction x, of a first stent spring (19) lies opposite a longer pointed arch (25a, 25c), facing toward the distal direction y, of a second stent spring (18) arranged thereafter in the proximal direction x, at a distance and in an imaginary line 90 that is parallel to the longitudinal axis of the vascular implant 10.

Returning to FIG. 2A, which shows the embodiment of a vascular implant according to the invention in a spatial representation (for the sake of clarity, the implant material connecting the stent springs is not shown in FIG. 2A): FIG. 2A also reveals that the stent spring has two set-up pointed arches 30, which because of the way in which they are shaped laterally protrude at an angle with respect to the longitudinal axis/direction of the vascular implant 10. The other pointed arches 20 of all the stent springs 12, 13, 14, 15, 16, 17, 18 and 19 run parallel to the longitudinal axis of the vascular implant 10. This protruding or setting up of the pointed arches 30 of the stent spring 14 has the effect of defining a side body or side branch 32; this side branch 32 offers an anchoring zone in the side vessel for a stent graft/stent-graft portion, for example a covered stent graft/stent-graft portion, which is inserted into a side vessel branching off from a main blood vessel (see FIG. 3A).

In the example shown in FIGS. 2A and 2B, the side body 32 also has a side-body stent spring 34 of its own, which consequently does not form a stent spring of the main body 44 of the vascular implant 10. The side-body stent spring 34 is indirectly connected by a side-body implant material 36 to the set-out pointed arch 30 of the stent spring 14 of the main body 44.

In the example shown in FIGS. 2A and 2B, the stent springs 12 to 19 and the side-body stent spring 34 are sewn onto the implant material 43 and 36, respectively.

FIGS. 2A and 2B also show that the pointed arches 20 of the individual stent springs 12 to 19 are arranged phase-offset with respect to the stent spring 12 to 19 respectively arranged thereafter, so that a vertex 24 of a first stent spring, at an imaginary line perpendicular in the longitudinal axis 12, is followed in by a further vertex 24 or a lowest point 45 of the stent spring 13 arranged thereafter, but these are offset obliquely with respect to one another.

Figure 3A:
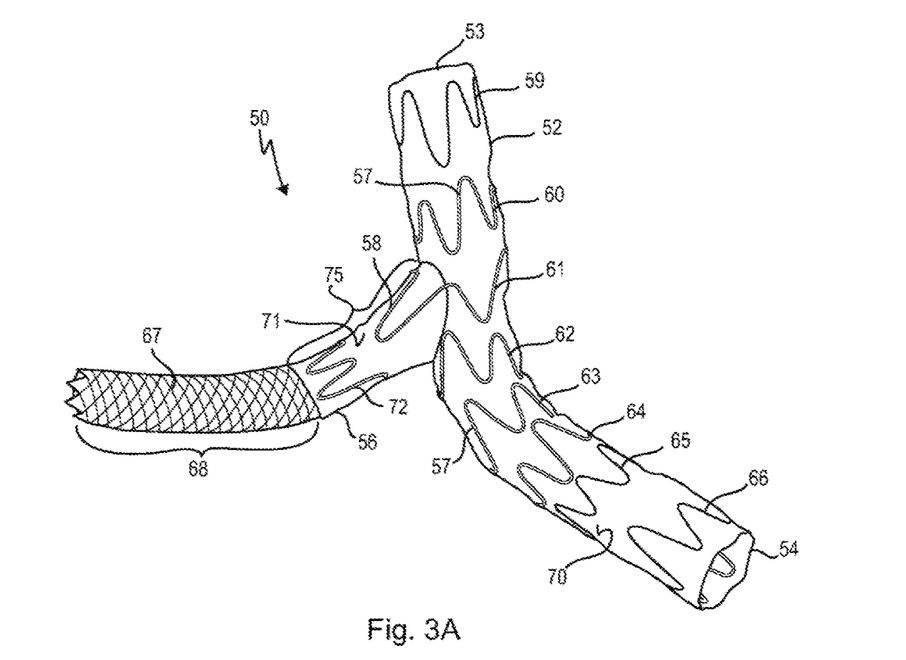
FIGS. 3A and 3B show a further embodiment of the vascular implant according to the invention, with the main body in various bent positions (FIGS. 3A and 3B)
Figure 3B:
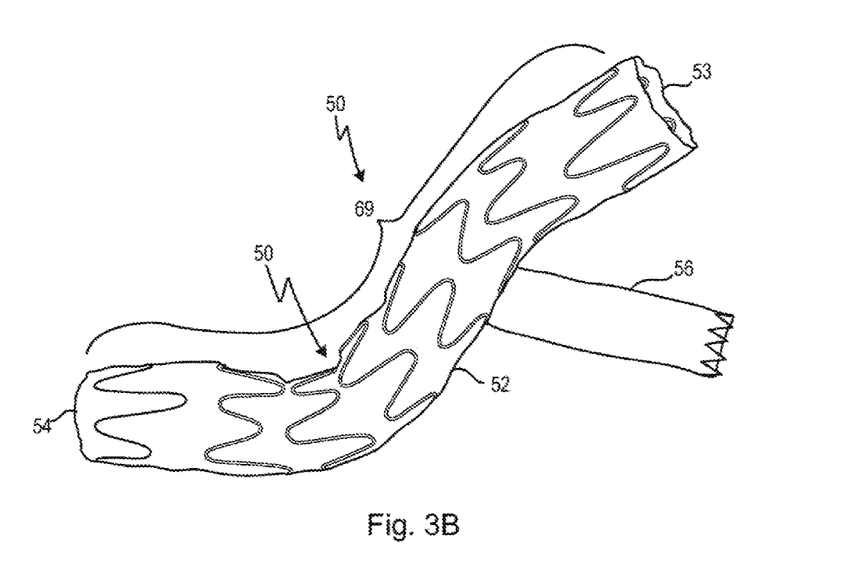

FIGS. 3A and 3B show a further embodiment of a vascular implant 50 according to the invention, likewise comprising a main body 52, a proximal end 53 and a distal end 54.

The vascular implant 50 shown in different bending positions in FIGS. 3A and B also has a side body 56, which is formed by two set-up pointed arches 58 of a stent spring 61 (only one that is set out can be seen).

The main body 52 of the vascular implant 50 has altogether eight stent springs 59, 60, 61, 62, 63, 64, 65, 66 with pointed arches 57 circumferentially meandering, and therefore has altogether a portion 69 which, due to the supporting stent springs 59 to 66, is regarded/referred to as stented. The side body or branch 56 has a side-body stent spring 72 of its own, and also a portion 68 supported by a stent wire mesh 67. Both the main body 52 of the vascular implant 50 and the side body 56 thereof respectively have an implant material, in FIGS. 3A and 3B the implant material of the main body 52 being denoted by 70 and the implant material of the side body 56 being denoted by 71.

FIGS. 3A and B also reveal that the side body 56 has along with a stented side-body portion 75 the further portion 68, in the case of which the implant material 71 is supported by the stent wire mesh 67. In this portion 68, the side-body implant material 71 may be different from the side-body implant material 71 in the stented portion 75 of the side body 56, and can be, for example, more dense, more solid or produced from a different material.

This side-body portion 75 of stent wire mesh 67 and implant material 71 represents a covered stent graft, which is preferably only implanted into this position in vivo, that is to say once the main body 52 has already been implanted into the main vessel.

Similarly, according to another embodiment, the main body 44 or 52 of the vascular implant 10, 50 may have a further portion that is supported by a stent wire mesh, or else is altogether unstented, and formed only from implant material, or else only comprises a stent wire mesh.

FIGS. 3A and B or the vascular implant 50 according to the invention that is shown in FIGS. 3A and B show that, due to the protruding pointed arches (only one can be seen) 58 of the stent spring 61 of the main body 52, the side body 56 of the vascular implant 50 as a whole protrudes at an angle from the longitudinal axis of the main body 52.

As already mentioned further above, here, too, the angle with which the side body 56 protrudes from the main body 52 is flexible and freely selectable, and can be chosen depending on the blood vessel branching off or on its angle. Preferred angles are angles in the range between 35° and 90°, and in particular angles in the range of 40° to 50°, and even more preferred in the range between 44° and 46°.

In FIGS. 3A and 3B, the shown embodiment of the vascular implant 50 according to the invention is in a bent state of the main body 52, it being evident here that, due to the asymmetrical formation of the phases and due to the stent springs 59, 60, 61, 62, 63, 64, 65, 66 being offset with respect one another, kinking in the region of an implant bend 74 is avoided. The bending radius (flexibility) which can be achieved is significantly smaller than in the case of symmetrical stent springs, while retaining the same longitudinal stability.

Figure 4A:
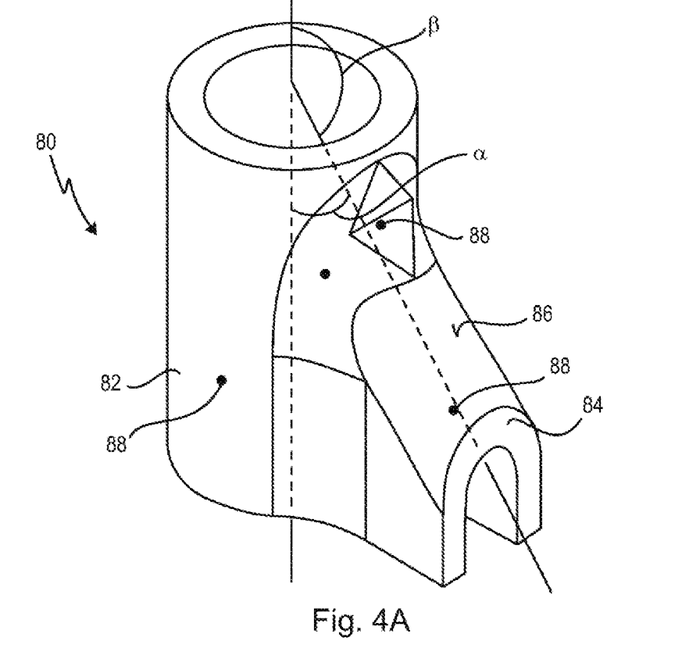
FIGS. 4A and 4B show a fitting, by means of which the stent spring with a set-up pointed arch is produced (FIG. 4A); a stent spring of a vascular implant according to the invention, as it was formed with a set-up pointed arch on the fitting from FIG. 4a (FIG. 4B)

Finally, in FIG. 4A, reference number 80 denotes a fitting, which has a cylindrical main body 82 and a fitting element 84, which protrudes at an angle from the cylindrical main body 82 and which is connected to the cylindrical main body 82. The fitting element 84 protrudes in relation to the longitudinal axis of the cylindrical main body 82 with an angle and forms a rounded inclined surface 86, the inclination of which with respect to the cylindrical main body 82 is denoted by the angle. The fitting also has pin-like or pin-shaped elements 88, which are intended for the forming the waves or pointed arches 20, 30, circumferentially meandering, for example of the stent spring 14 (see FIG. 4B).

Figure 4B:
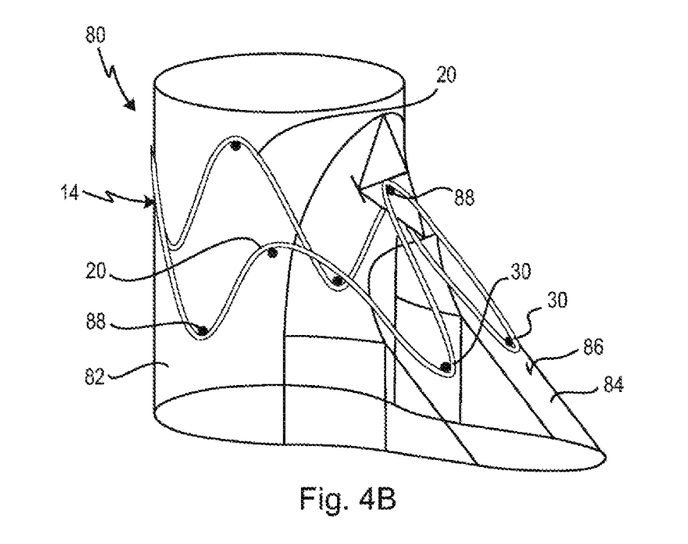

For forming of a vascular implant 10, 50 according to the invention, the fitting 80 is used in such a way that the stent spring that has at least one, preferably at least two, set-out pointed arch (pointed arches) 30 or 58 (see FIG. 4B) is formed on it. In FIG. 4B, the fitting is shown transparently for better overall clarity. To form a stent spring 14, for example a metal wire with a shape-memory property, for example of nitinol, is passed in the cold state around the pin-shaped elements 88 of the cylindrical main body 82, circumferentially meandering in loops, in order to form the pointed arches 20. The set-up pointed arch 30 is formed by placing it over the inclined surface 86 of the fitting element 84 and passing it over the pin-shaped elements 88. The wire is fixed and subsequently subjected to a heat treatment, in order to fix the meandering form.

After curing of the heated material, the stent spring thus formed retains its form, which represents the expanded state of the stent spring.

The stent spring thus formed is placed at the desired location in the vascular implant 10, 50, and, thus, at the point of the vascular implant 10, 50 from which the at least one side body 32, 56 of the vascular implant 10, 50 is intended to be set up.

What is claimed is:

1. A vascular implant for implanting into a blood vessel of a patient, the vascular implant being transformable from a compressed state into a self-expanded state, the vascular implant comprising:
    a hollow-cylindrical main body with a proximal end and a distal end, the hollow-cylindrical main body defining a main body lumen and a longitudinal axis;
    at least one hollow-cylindrical side body that branches off from the main body and comprises a side body lumen and a side body implant material, the side body lumen being in fluidic connection with the main body lumen;
    a plurality of stent springs successively arranged over the longitudinal axis of the main body, the plurality of stent springs including a first stent spring, a second stent spring, and a protruding stent spring;
    an implant material fixed to the plurality of stent springs and connecting them, the stent springs being connected to one another via the implant material only and not connected by any other means between adjacent springs,
    wherein the first stent spring, the second stent spring, and the protruding stent spring each have a plurality of legs and pointed arches, the pointed arches being defined by respective adjacent legs and a vertex or depression between the respective adjacent legs such that the pointed arches of the first and the second stent springs alternately face toward the proximal end and the distal end of the main body and parallel to the longitudinal axis thereof,
    wherein at least three consecutive legs of each of the first stent spring, the second stent spring, and the protruding stent spring have different lengths, the at least three consecutive legs connecting a first vertex, a first depression following the first vertex in a circumferential direction, a second vertex following the first depression in the circumferential direction, and a second depression following the second vertex in the circumferential direction,
    wherein respective vertices of the first stent spring are aligned circumferentially with respective depressions of the second stent spring and respective depressions of the first stent spring are aligned circumferentially with respective vertices of the second stent spring,
    wherein the first stent spring, the second stent spring, and the protruding stent spring have an asymmetrical shape in which successive vertices have different heights in the proximal direction along the longitudinal axis and successive depressions have different depths in the distal direction along the longitudinal axis,
    wherein the vertices of the first stent spring, the second stent spring, and the protruding stent spring include at least one maximum-height vertex that has a maximum height of respective vertices and the depressions of the first stent spring, the second stent spring, and the protruding stent spring include at least one maximum-depth depression that has a maximum depth of respective depressions,
    wherein, in the self-expanded state, the at least one side body branching off from the main body is set up at an angle in relation to the longitudinal axis of the main body, the angle being defined by at least one pointed arch of the protruding stent spring of the main body, the at least one pointed arch angularly protruding in a preformed way in relation to the longitudinal axis of the main body in the self-expanded state, and
    wherein the at least one pointed arch is formed by one of the at least one maximum-depth depressions of the protruding stent spring.

2. The vascular implant as claimed in claim 1, wherein the angle is between 20° and 90°.

3. The vascular implant as claimed in claim 1, wherein the at least one side body has a first side-body portion with at least one side-body stent spring circumferentially meandering and the side body implant material fixed to and connecting the side-body stent spring and the protruding stent spring of the main body, the at least one side-body stent spring and the protruding stent spring of the main body only being connected via the side body implant material and not connected by any other means between adjacent springs.

4. The vascular implant as claimed in claim 3, comprising at least one portion that does not have any stent springs or that has a braided or lasered stent, the at least one portion adjoining, proximally or distally, one of the stent springs of the main body or the at least one side-body stent spring of the at least one side body.

5. The vascular implant as claimed in claim 1, wherein at least two stent springs arranged successively with respect to the longitudinal axis of the hollow-cylindrical main body and with respect to one another, such, that the vertices of the pointed arches of the first stent spring, respectively, lie opposite to the depressions of the pointed arches of the second stent spring arranged thereafter over the longitudinal axis of the vascular implant at a distance from one another and in a line that is parallel to the longitudinal axis of the vascular implant.

6. The vascular implant as claimed in claim 1, wherein the side body implant material is sewn to the implant material of the main body.

7. The vascular implant as claimed in claim 1, wherein the stent springs of the main body and/or of the side body are fixed on the inside or on the outside to the implant material of the hollow-cylindrical main body and/or of the side body.

8. The vascular implant as claimed in claim 1, wherein the at least one side body comprises between one and four side bodies branching off at the angle.

9. The vascular implant as claimed in claim 1, wherein the angle is between 35° and 55°.

10. The vascular implant as claimed in claim 1, wherein the angle is 45°.

11. A vascular implant for implanting into a blood vessel of a patient, the vascular implant being transformable from a compressed state into a self-expanded state, the vascular implant comprising:
    a hollow-cylindrical main body with a proximal end and a distal end, a main body lumen and a longitudinal axis, and comprising a portion that has, respectively, a plurality of one-piece stent springs successively arranged over the longitudinal axis of the main body and circumferentially meandering, respectively, perpendicularly in relation to the longitudinal axis, the plurality of one-piece stent springs including at least two stent springs and a protruding stent spring;

an implant material fixed to the stent springs and connecting them, the stent springs being connected to one another via the implant material only and not connected by any other means between adjacent springs; and at least one hollow-cylindrical side body that branches off from the main body and comprises a side body lumen and a side body implant material, the side body lumen being in fluidic connection with the main body lumen, wherein the circumferentially meandering stent springs have pointed arches that alternately face toward the proximal end and the distal end of the main body and parallel to the longitudinal axis thereof, wherein the at least two stent springs and the protruding stent spring have legs of different lengths such that successive pointed arches facing the proximal end vary in height circumferentially in the proximal direction along the longitudinal axis and successive pointed arches facing the distal end vary in depth circumferentially in the distal direction along the longitudinal axis, the pointed arches of the at least two stent springs and the protruding stent springs are formed by two legs and a vertex or depression lying between the legs and have one or more pointed arches, respectively, that have a maximum depth and a maximum height, wherein a first pointed arch of a first stent spring facing toward the proximal end lies opposite a second pointed arch of an adjacent second stent spring facing toward the distal end along a first imaginary line that is parallel to the longitudinal axis of the vascular implant, and/or wherein a second pointed arch of the first stent spring facing toward the proximal end lies opposite a first pointed arch of the adjacent second stent spring facing toward the distal end along a second imaginary line that is parallel to the longitudinal axis of the vascular implant, wherein, in the self-expanded state, the at least one side body branching off from the main body forms an angle relative to the longitudinal axis of the main body, the angle being defined by at least one pointed arch of the pointed arches of the protruding stent spring, the protruding stent spring angularly protruding in a preformed way in relation to the longitudinal axis of the main body in the self-expanded state, and wherein the at least one pointed arch of the protruding stent spring has the maximum depth.

* * * * *